United States Patent [19]

Radford et al.

[11] Patent Number: 5,955,270
[45] Date of Patent: Sep. 21, 1999

[54] EXPLOITATION OF THE CELLULASE ENZYME COMPLEX OF NEUROSPORA

[75] Inventors: Alan Radford, Homforth; John Howard Parish, Harrogate, both of United Kingdom

[73] Assignee: The University of Leeds, Leeds, United Kingdom

[21] Appl. No.: 08/676,166

[22] PCT Filed: Jan. 11, 1995

[86] PCT No.: PCT/GB95/00049

§ 371 Date: Jul. 15, 1996

§ 102(e) Date: Jul. 15, 1996

[87] PCT Pub. No.: WO95/19441

PCT Pub. Date: Jul. 20, 1995

[30] Foreign Application Priority Data

Jan. 14, 1994 [GB] United Kingdom .................. 9400623

[51] Int. Cl.[6] .............................. C12Q 1/68; C12N 15/63; C07K 13/00; C07H 21/04
[52] U.S. Cl. .......................... 435/6; 435/69.1; 435/320.1; 435/197; 530/350; 536/23.1
[58] Field of Search ................................ 435/6, 29, 69.1, 435/91.1, 201, 235.1, 254.4, 320.1, 197; 536/23.2, 23.4, 24.1, 23.74, 24.2, 23.1; 530/350

[56] References Cited

U.S. PATENT DOCUMENTS 5,340,731  8/1994  Kilburn et al. ......................... 435/179
5,503,991  4/1996  Gwynne et al. ........................ 435/69.1
5,686,593  11/1997 Woldike et al. ........................ 536/23.1

FOREIGN PATENT DOCUMENTS

| 0137280 | 4/1985 | European Pat. Off. . |
| 0244234 | 11/1987 | European Pat. Off. . |
| WO 90/00609 | 1/1990 | WIPO . |
| WO 91/13971 | 9/1991 | WIPO . |

OTHER PUBLICATIONS

Stone et al. (1993) Biol. Abst. 96:550 (#123940).

Stone et al. (1993) Curr. Genet. 24:205–11.

Azevedo et al. (1991) Biol. Abst. 91:445 (#61402).

Azevedo et al. (1990) J. Gen. Microbiol. 136:2569–76.

Yazdi et al. (1990) Enz. Microb. Technol. 12:120–3.

Sims et al. (1988) Gene 74:411–22.

*Primary Examiner*—James Ketter
*Assistant Examiner*—William Sandals
*Attorney, Agent, or Firm*—Klauber & Jackson

[57] ABSTRACT

The invention relates to the gene encoding the enzyme cellobiohydrolase-1. Specifically, the invention concerns the elucidation of the regulatable promoter sequence of said gene and the subsequent genetic manipulation of said sequence so as to combine it with DNA sequence structure of a heterologous peptide in order to provide for selective expression of heterologous peptide in accordance with the expression features of the promoter.

4 Claims, 10 Drawing Sheets

FIG. 1A

```
gagtctgtaaccaaactctttaccgtcctgggtccctgtagcagtatatccattgttt          60 cttatataaggttaggggtaaatcccggcgctcatgactcgcctttcccttatct            120 gatcgggcaccggaaaccaattgcactcaaaATGAGGGCCTCGCTCCTGGCCTTCTCCCT       180
                                 M  R  A  S  L  L  A  F  S  L
Sau3A AAAVAGGQQAG TLTAKRHPS
GCTGCCGCCGTGGCCGGCGGCCAGCAGGCCGGCACTCTCACCGCCAAGAGGCACCCATC        240
 A  A  A  V  A  G  G  Q  Q  A  G  T  L  T  A  K  R  H  P  S L  T  W  Q  K  C  T  R  G  G  C  P  T  L  N  T  T  M  V  L
CTCACATGGCAGAAGTGCACCAGGGGGGGTGCCCGACCCTGAACACCACGATGGTGCT        300
                                              ApaLI D  A  N  W  R  W  T  H  A  T  S  G  S  T  K  C  Y  T  G  N
CGACGCGAACTGGCGCTGGACTCACGCCACGTCCGGCTCCACGAAGTGCTACACGGGCAA      360

K  W  Q  A  T  L  C  P  D  G  K  S  C  A  A  N  C  A  L  D
CAAGTGGCAGGCGACGCTCTGCCCCGATGGCAAGTCGTGCGCGGCGAACTGCGCGCTGGA      420

G  A  D  Y  T  G  T  Y  G  I  T  G  S  G  W  S  L  T  L  Q
CGGCGCCGACTACACCGGCACCTACGGGATCACCGGGAGCGGCTGGTCCCTCACGCTCCA      480
                                 Sau3A

F  V  T  D  N  V  G  A  R  A  Y  L  M  A  D  D  T  Q  Y  Q
GTTCGTCACGGACAACGTCGGGGCCCGTGCCTACCTGATGGCCGACGACACGCAGTACCA      540
```

FIG. 1B

```
  M   L   E   L   L   N   Q   E   L   W   F   D   V   D   M   S   N   I   P   C
GATGTTGGAGCTCCTGAACCAGGAGTTGTGGTTCGACGTCGATATGTCGAACATCCCGTG     600
           SacI                              AatII

G   L   N   G   A   L   Y   L   S   A   M   D   A   D   G   G   M   R   K   Y
CGGTCTGAACGGGGCCCTCTACCTCTCGGCGATGGACGCGGATGGGGGCATGAGGAAGTA     660

P   T   N   K   A   G   A   K   Y   A   T   G   Y   C   D   A   Q   C   P   R
CCCGACCAACAAGGCTGGCGCTAAGTACGCTACCGGTTACTGCGACGCTCAGTGCCCCCG     720
                     PCR primer ->

D   L   K   Y   I   N   G   I   A   N   V   E   G   W   T   P   S   T   N   D
TGATCTCAAGTACATCAACGGTATCGCCAACGTTGAGGGCTGAGACCCCTTCCACCAACGA    780
  Sau3A

A   N   G   I   G   D   H   G   S   C   C   S   E   M   D   I   W
TGCTAACGGTATTGGTGACCACGGATCTTGCTGCTGCTCTGAGATGGATATCTGGgtttgttt  840
                                  Sau3A E   A   N
gccgatttcctttcatcattagcatcacaggtaactaacacccacctaagGAAGCGAAC       900

K   V   S   T   A   F   T   P   H   P   C   T   T   I   E   Q   H   M   C   E
AAAGTCTCTACAGCGTTCACCCCGCACCCCTGCACCACCATCGAACAGCACATGTGCGAG     960
```

FIG.1C

```
    G   D   S   C   G   G   T   Y   S   D   D   R   Y   G   V   L   C   D   A   D
GGTGACTCCTGCGGTGGTACCTATTCCGACGACCGCTATGGCGTACTTTGCGATGCCGAT 1020
                        KpnI

G   C   D   F   N   S   Y   R   M   G   N   T   T   F   Y   G   E   G   K   T
GGTTGTGACTTCAACAGTTACCGCATGGGCAACACCACCTTCTACGGTGAGGGCAAGACT 1080

V   D   T   S   S   K   F   T   V   V   Q   F   I   K   D   S   A   G   D
GTCGATACCAGCTCCAAGTTCACCGTTGTCCAGTTCATCAAGGACTCCGCTGGCGAT 1140
                                                            Sau3A

L   A   E   I   K   A   F   Y   V   Q   N   G   K   V   I   E   N   S   Q   S
CTTGCTGAGATCAAGGCCTTCTACGTCCAGAACGGAAAAGTCATTGAGAACTCTCAGTCC 1200
    Sau3A

N   V   D   G   V   S   G   N   S   I   T   Q   S   F   C   K   S   Q   K   T
AACGTTGATGGAGTTTCTGGCAACTCCATCACCCAGTCTTTCTGCAAGTCTCAGAAGACT 1260

A   F   G   D   I   D   D   F   N   K   K   G   G   L   K   Q   M   G   K   A
GCTTTCGGCGATATCGATGACTTCAACAAGAAGGGTGGCCTGAAGCAAATGGGCAAGGCC 1320
                ClaI

L   A   Q   A   M   V   L   V   M   S   I   W   D   D   H   A   A   N   M   L
CTTGCCCAAGCCATGGTCCTCGTCATGTCCATCTGGGACGACCATGCCGCCAACATGCTC 1380
                NcoI
```

FIG.1D

```
  W  L  D  S  T  Y  P  V  P  K  V  P  G  A  Y  R  G  S  G  P
TGGCTCGACTCCACCTACCCTGTCCCGAAGGTCCCCGGTGCTTACCGTGGCAGTGGCCCT  1440

T  T  S  G  V  P  A  E  V  E  A  N  A  P  N  S  K  V  A  F
ACCACCTCGGGTGTCCCAGCTGAGGTCGACGCCAATGCTCCCAACTCCAAGGTCGCCTTC  1500
                              SalI                    <- PCR primer S  N  I  K  F  G  H  L  G  I  S  P  F  S  G  G  S  S  G  T
TCCAACATCAAGTTCGGCCACCTCGGGATCTCTCCTTTTAGCGGGGGCTCTTCCGGCACC  1560
                                    Sau3A P  P  S  N  P  S  S  A  S  P  T  S  S  T  A  K  P  S  S
CCTCCTTCCAACCCTTCGAGCTCCGCAAGCCCGACTTCCTCCACTGCTAAGCCTTCTTCC  1620
                          SacI T  S  T  A  S  N  P  S  G  T  G  A  A  H  W  A  Q  C  G  G
ACCTCTACTGCCTCCAACCCCAGCGGTACCGGTGCTGCTCACTGGGCTCAGTGCGGTGGT  1680

I  G  F  S  G  P  T  T  C  P  E  P  Y  T  C  A  K  D  H  D
ATTGGCTTCTCTGGCCCCACCACTTGCCCAGAGCCCTACACTTGCGCAAAAGATCACGAC  1740

I  Y  S  Q  C  V  *
ATTTACTCCCAGTGCGTGTAAattactagcctgctaggtaacctttggttcctctac     1800 tacggcagctaggtgaactgcgactgcgaagcaaaaaggaacttcgagaa
```

```
               210       220       230       240       250       260       270       280       290       300
NCRX    QCPRDLKYINGIANVEGWTPSTNDAN-GIGDHGSCCSEMDIWEANKVSTAFTPHPCTTIEQHMCEGDSCGGTYSDDRYGVLCDADGCDFNSYRMGNTTFY
        ****.*.****|****|******.* .*|||*.********************..*|.****|******|***. .**. .*. .*************|***
HGRX    QCPRDIKFINGEANIEGWTGSTNDPNAGAGRYGTCCSEMDIWEANNMATAFTPHPCTIIGQSRCEGDSCGGTYSNERYAGVCDPDGCDFNSYRQGNKTFY
        ****|*********.****..*.****.*  |*. ************.*.*******|| *.****|******|*..****..*.|****|***|****
TRRX    QCPRDLKFINGQANVEGWEPSSNNANTGIGHGSCCSEMDIWEANSISEALTPHPCTTVGQEICEGDGCGGTYSDNRYGGTCDPDGCDWNPYRLGNTSFY
        ****|*********|******.****.*******************************|********|******|************************
TRVX    QCPRDLKFINGQANVEGWEPSSNNANTGIGHGSCCSEMDIWEANSISEALTPHPCTTVGQEICEGDSCGGTYSGDRYGGTCDPDGCDWNPYRLGNTSFY
        ***.||...|**.|*.                 .|.*|****.|****.***.                  **..|||**|.*.*
TRRN    QCP-VQTWRNGTLNT----------------SHQGFCCNEMDILEGNSRANALTPHSCTATA------------CDSAGCGNFPYGSGYKSYY
        ***..  .*...                       *..*.  .*.**.                          *.........*  .. .
PHCX    QCPRDIKFINGEANVEGWNATSANAGT--GNYGTCCTEMDIWEANNDAAAYTPHPCTTNAQTRCSGSDCT------RDTGLCDADGCDFNSFRMGDQTFL 310       320       330       340       350       360       370       380       390       400
NCRX    GEGK---TVDTSSKFTVVTQFIKDSA------GDLAEIKAFYVQNGKVIENSQSNVDGVSG-NSITQSFCKSQKTAFGDIDDFNKKGGLKQMGKALAQAMVLVM
        *.*. .*. .**********|****. |                 .**** .***.*.  |.***|.******|****************.*****|******
HGRX    GKGM---TVHTTKKITVVTQFLKDAN------GDLGEIKRFYVQDGKIIPNSESTIPGVEG-NSITQDWCDRQKVAFGDIDDFNRKGGMKQMGKALAGPMVLVM
        |||   *|.*.******.**|                 |||..*..*..*.|.*.  *.****.*...**|.*.*.*
TRRX    GPGSSFTLDTTKKLTVVTQF------------ETSGAINRYYVQNGVTFQQPNAELGSYSG-NELNDDYCTAEEAEFGGSSFSDK-GGLTQFKKATSGGMVLVM
        ****.***************                ***.***.******|****************************************************
TRVX    GPGSSFTLDTTKKLTVVTQF------------ETSGAINRYYVQNGVTFQQPNAELGDYSG-NSLDDDYCAAEEAEFGGSSFSDK-GGLTQFKKATSGGMVLVM
        ****.*******.*******.       ||...|                        .           ...*. ..  |               **.*****.|
TRRN    GPGD---TVDTSKTFTIITQFNTDNGSPSGNLVSITRKYQQNGVDIPSAQ---------PGGDTISSCPSA-SAY-----------GGLATMGKALSSGMVLVF
        *.*     ****.********.*.*.***                     |.*           **     .*.            ****.*****.*****.
PHCX    GKGL---TVDTSKPFTVVTQFITNDGTSAGTLTEIRRLYVQNGKVIQNSSVKIPGIDPVNSITDNFCSQQKTAFGDTNYFAQHGGLKQVGEALRTGMVLAL
```

FIG. 3C

```
             410        420        430        440        450        460        470        480        490        500
NCRX  SIWDDHAANMLWLDSTYPVPKV---PGAYRGSGPTTSGVPAEVEANAPNSKVAFSNIKFGHLGISPFSGGSSGTPPSNPSSSASPTSSTAKPSSTSTASN
      *****************.**  .  |.***.**.|.******************.**|. . ||..*|..**.. .**..|.*..|*
HGRX  SIWDDHASNMLWLDSTFPVDAAGK-PGAERGACPTTSGVPAEVEAEAPNSNVVFSNIREGPIGSTVAGLPGAGNGGNNGGNPPPTTTTSSAPATTTAS
      *..****||.|.*.**.*.  .  . *** .**.*.*.*.*.**.****  .. .*|.*****  || |*||.|****..||******|.*
TRRX  SLWDDYYANMLWLDSTYPTNETSSTPGAVRGSCSTSSGVPAQVESQSPNAKVTFSNIKFGPIGSTGNPSGGNPPGNRG------TTTTRRPATTTGSS
      *..****************|******.******.*|*****.*..*.*****.*.*****.*******.*****       ****.****.****
TRVI  SLWDDYYANMLWLDSTYPTDETSSTPGAVRGSSTSSGVPAQLESNSPNAKVVYSNIKFGPIGSTGNPSGGNPPGGNPPG------TTTPRPATSTGSS
      *.*.| |||.*.****  .  .    *    .   .*.||.*..  . |.*.*..****.* .||**    .|| .        .*|.  ..*.**
TRRN  SIWNDNSQYMNWLDS---------GNA-GPCSSTEGNPSNILANNPNTHVVFSNIRWGDIGSTTNSTAPPPPASS------TTFSTTRRSSTTSSS
      ****.*.                . * .   .  *..  .*.*.  *..****  *.***..*.. .        .  .*     .
PHCX  SIWDDYAANMLWLDSNYPTNKDPSTPGVARGTCATTSGVPAQIEAQSPNAYVVFSNIKFGDLNTTYTGTVSSSSVSSHSSTSTSSSHSSSSTPPTQPTG 510        520        530        540
NCRX  PSGTGAAHWGLQCGGIGFSGPTTCPEPYTCAKDHDIYSQCV
      . |. .*  |   ****.* .* ***|*.  *.*.****.
HGRX  AGPKAG-RWQ-QCGGIGFTGPTGPTQCEEPYICTKLNDWYSQCL
      .**  .  |    ****..*.*.****..* || *..****
TRRX  PGPTQS-HYG-QCGGIGYSGPTVCASGTTCQVLNPYYSQCL
      ****   .. | ******|***.*****|************
TRVI  PGPTQT-HYG-QCGGIGYIGPTVCASGSTCQVLNPYYSQCL
      *.**   .** *|******|***.*****|.||*|******
TRRN  PSCTQT-HWG-QCGGIGYTGSTTCSGTTCQYSNDYYSQCL
      *      *** *******..*..****. * ******
PHCX  VTVPQ---WG-QCGGIGYTGSTTCASPYTCHVLNPYYSQCY
```

EXPLOITATION OF THE CELLULASE ENZYME COMPLEX OF NEUROSPORA

The invention relates to a method and recombinant means particularly, but not exclusively, expression cassettes and expression/export cassettes for the production of heterologous peptides and the enhanced production of cellulases especially cellobiohydrolase-1. The method and means have particular application in the production of such peptides and enzymes from the biotechnological exploitation of filamentous fungi and particularly *Neurospora crassa.*

The most abundant cell-wall and structural polysaccharide in the plant world is cellulose. Cellulose is a linear polymer of D-glucose arranged in a Beta 1–4 linkage. Cellulose is a major component of wood and thus of paper, it is also a major component of cotton and other plant materials.

On complete hydrolysis, cellulose is broken down to D-glucose, but partial hydrolysis yields a reducing disaccharide cellobiose in which the linkage between the D-glucose units is a glycosidic Beta 1–4 arrangement. Enzymes capable of hydrolysing cellulose are not secreted in the digestive tract of most mammals and therefore cellulose is not a source of food. However, ruminants can use celluloses as food because in the rumen of their stomachs they house bacteria which produce the enzyme cellulase.

As fossil fuel reserves become depleted, a renewable feed-stock for the chemical industry becomes more significant The obvious renewable resource is cellulose, which is already in embarrassingly large supply and largely wasted. However, the conversion of cellulose to a more readily utilisable substance such as sugars and alcohols is problematical.

*Neurospora crassa* grows well on cellulosic substrates. In doing so, it secretes enzymes of the cellulase complex, hydrolysing the substrate outside the cell. The resulting soluble sugars may be recovered before they are taken up by the cell and further metabolised. The amount of cellulose/cellobiose typically required to activate gene expression is represented by 1–2% by weight of cellulose/cellobiose.

The cellobiohydrolase-1 enzyme of *Neurospora crassa* is the major enzyme in the cellulase complex, and one of the major exported proteins of the organism when induced by cellulose or cellobiose (the product of partial hydrolysis of cellulose). Furthermore, *Neurospora crassa* is a very efficient cellulolytic species, able to hydrolyse cellulose efficiently, and grow on it as the sole carbon source. We have grown it on a range of cellulosic substrates, including pressed-sugar-beet pulp, cereal straw and spent malted grains from breweries. Indeed, Neurospora has been isolated in the wild from burnt sugar cane, and so is likely to grow well on bagasse from sugar cane processing. In addition, it grows very well on starch and a wide range of soluble sugars. Its nitrogen requirement for growth is readily satisfied by the supply of any one of a wide range of nitrogen sources, including protein, amino acids, ammonium ions, nitrate, nitrite, and urea. Its only complex biochemical requirement is for trace amounts of the vitamin biotin.

It follows from the above that genetic manipulation of the gene encoding the promoter and associated enzyme sequence structure for the enzyme cellobiohydrolase-1 will enable us to do a number of things, namely:

a) Increase the level of cellobiohydrolase-1 enzyme either by increasing the copy number of the cbh-1 gene or increasing the strength of the promoter of the cbh-1 gene. Both of these ways could be achieved by transforming in either additional copies or an altered copy of the gene, or possibly both. Thus for example, one could produce by transformation multiple copies of the gene encoding the cellobiohydrolase-1 enzyme so as to increase the level of cellobiohydrolase-1 production.

b) Alternatively, one could, by further manipulation, increase the strength of the cellobiohydrolase promoter thus increasing the level of cellobiohydrolase-1 enzyme.

c) Attach a suitable heterologous gene to the cellobiohydrolase promoter thus ensuring that such gene is transcribed by cellulose- or cellobiose-induction and at the high rate that the enzyme cellobiohydrolase would normally be produced, resulting in the production of high levels of the heterologous gene product The expression constructs are of the following types;

1) A transcriptional fusion, including the cbh-1 promoter and regulatory sequences upstream from a multiple cloning site, to allow the construction of transcriptional fusions with the coding sequence of any desired heterologous peptide. Such production would be intracellular, requiring subsequent purification of the product from the cell extract.

2) A translational fusion, including the cbh-1 promoter an export signal peptide in transitional fusions (in all three possible reading frames) with the coding sequence of the desired heterologous peptide.

3) A translational fusion of a heterologous peptide near the C-terminus of the cbh-1 gene, with a proteolytic cleavage site in a linking region to allow subsequent cleavage of the heterologous peptide from the cbh-1. This would exploit the dispensable hinge and cellulose-binding domain cbh-1 replacing this region with the other peptide.

There is a further advantage to be gained from manipulating the gene encoding the cellobiohydrolase-1 enzyme in that the c-terminal end of the enzyme comprises a cellulose-binding domain. Genetic manipulation such that this domain is spliced onto any enzyme would confer on such enzyme cellulose-binding properties. This could be exploited in at least two ways. Firstly, the cellulose-binding domain could be used to immobilise a chosen heterologous protein onto a cellulose matrix. This would in turn facilitate biocatalysis by subsequently exposing the matrix to an appropriate substrate. Secondly, the use of the cellulose-binding domain could be exploited for purification means. For example, any desired heterologous protein having attached thereto a cellulose-binding domain could be bound to a cellulose matrix during the process of purification. Further, the process of purification could be taken one step further by specific protolytic cleavage at a site between the desired protein and the cellulose-binding domain so releasing the desired protein but leaving the cellulose-binding domain attached to the matrix. The cellulose-binding domain of *Neurospora crassa* is suitable for this type of purification because it is known to be a relatively small and efficient binding domain.

There are at least two possible genetic constructs:

1) a cloning construct with a cloning site in or n-terminal to the hinge region that is the region between the heterologous catalytic domain and the cellulose-binding domain. It is possible to insert coding sequence for a heterologous peptide in a translational fusion immediately upstream from the hinge and cellulose-binding domain. With a suitable promoter, expression of the fusion protein can be achieved. If the heterologous peptide Is an enzyme, the fusion protein with this enzyme activity can be immobilised by allowing it to attach to a cellulose matrix. The enzyme substrate can then be passed over the immobilised enzyme and the product produced.

2) an extension of the above with a specific proteolytic cleavage site constructed in the (hinge) region between the heterologous catalytic domain and the cellulose-binding domain. This would permit a simple purification by specifically binding the fusion protein to the cellulose matrix while washing all others off, and then specifically cleaving with the protease to release the heterologous moiety of the fusion protein from the still-bound cellulose-binding domain.

The term heterologous gene expression and heterologous protein is used in this document to mean the expression of proteins not present or common in the host.

Ideally the technology of the invention will be used to produce mammalian peptide hormones or any protein of pharmaceutical significance.

The genus Neurospora has several advantages for study with a view to its possible exploitation as a host for heterologous gene expression or enhanced cellulose production. These advantages are documented in copending application number PCT/GB 94/01789.

Here we report the DNA sequence of the cellobiohydrolase-1 gene, cbh-1, of *Neurospora crassa* together with flanking sequences and compare its amino acid sequence with other cellobiohydrolase-1 genes emanating from different organisms.

A full understanding of this gene, cbh-1, has enabled us to genetically engineer expression cassettes and expression/export cassettes containing high level, regulated promoter along with any other pre-selected gene sequence. The control of production of this gene sequence is in accordance with the repression induction features of the promoter. Thus we can selectively control the production of the said gene sequence according to the presence or absence of cellobiose or cellobiose.

It is apparent that this technology has great significance in the genetic engineering industry because it enables selected production of a pre-determined peptide in an extremely efficient and cost effective way without the production of secondary metabolites. Further, since Neurospora, like other filamentous ascomycete fungi, but unlike yeast, tends to glycosylate proteins in a way resembling that of mammals, there is a reasonable expectation that any heterologously produced mammalian peptide hormone sequences requiring glycosylation for biological activity will in fact be biologically active.

Further, since the cellobiohydrolase-1 enzyme has a cellulose-binding domain, it follows the pre-selected gene sequences which are attached to the promoter can be so engineered that they are also attached to the said cellulose-binding domain thus conferring cellulose-binding properties on the pre-selected peptide corresponding to the pre-selected gene sequence. This cellulose-binding property can be used during biocatalyis to ensure that the relevant enzyme is attached to cellulose matrix prior to the introduction of its relevant substrate. Further, cellulose-binding domain can be used as indicated above during purification procedures.

It is therefore an object of the invention to provide methods and means for facilitating the enhanced breakdown of cellulose, conferring cellulose binding properties on pre-selected heterologous peptides and providing a system for the efficient cellulose/cellobiose-induction of heterologous proteins.

According to a first aspect of the invention there is provided a regulated promoter having the DNA sequence structure shown in FIG. 1 (SEQ ID NO:1), or part thereof, or a functionally equivalent nucleotide sequence.

According to a second aspect of the invention there is provided a regulated promoter and an upstream activator having the DNA sequence structure shown in FIG. 1 (SEQ ID NO:1), or part thereof.

Preferably said DNA sequence structure encodes a protein, the amino acid sequence of which is depicted in FIG. 1 (SEQ ID NO:2) or a protein of equivalent biological activity having substantially the amino acid sequence depicted in FIG. 1 (SEQ ID NO:2).

According to a third aspect of the invention there is provided a regulated promoter as aforedescribed which is further provided with linkers whereby ligation of the promoter with a pre-selected gene encoding a desired protein is facilitated.

According to a fourth aspect of the invention there is provided a regulator promoter as aforedescribed which is further provided with linkers whereby ligation of the promoter with a pre-selected gene encoding a desired protein is facilitated and also a signal sequence to facilitate export of said desired protein from its host cell.

Preferably said linkers include restriction sites or enzyme recognition sites to facilitate subsequent cleavage.

According to a fifth aspect of the invention there is provided DNA sequence structure shown in FIG. 1 (SEQ ID NO:1), or part thereof, or a functionally equivalent nucleotide sequence, which also includes cloning sites and processing sites which preferably are located at the c-terminal cellulose binding domain of the enzyme.

According to a further aspect of the invention there is provided a vector or plasmid incorporating the aforementioned DNA sequence structures.

According to a yet further aspect of the invention there is provided an expression cassette including at least the aforementioned regulated DNA promoter sequence plus a linker.

Preferably the expression cassette also includes the upstream activator sequence.

Preferably further still said linker can be subsequently cleaved.

Preferably further still the expression cassette also includes the sequence structure encoding the cellulose-binding domain.

Preferably further still said expression cassette includes a Neurospora selectable marker.

Preferably further still said expression cassette contains a replication origin from, ideally, *E. Coli* and preferably also an *E. Coli* selectable marker, for example, a gene encoding ampicillin-resistance.

Preferably further still said expression cassette incorporates a multiple cloning site whereby insertion of any pre-selected gene sequence, homologous or heterologous, can be incorporated via transcriptional transfusion.

According to a yet further aspect of the invention there is provided an expression/export cassette which incorporates any one or combination of the aforementioned expression features and which further incorporates the DNA sequence structure encoding a secretion signal.

Preferably said expression/export cassette contains the aforementioned DNA sequence translationally fused to the coding sequence of the heterologous peptide.

Preferably three different expression/export cassettes would be constructed. The multiple cloning site oligonucleotide is in a different reading frame in each to permit in-frame translational fusion to the coding sequence for the heterologous peptide. This is achieved by appropriate design of the ends of the synthetic multiple cloning site oligonucleotide.

Although the provision of an expression/export cassette is advantageous in that it enables a heterologous peptide to be both expressed and then exported, it is limiting because only those peptides which are susceptible to secretion can be made in this way.

According to a yet further aspect of the invention there is provided a method for transforming filamentous fungus, and particularly *Neurospora crassa* comprising the insertion of at least one of the aforementioned expression cassettes and/or expression/export cassettes into same using recombinant techniques.

According to a yet further aspect of the invention there is provided a filamentous fungus including at least one expression cassette and/or expression/export cassette according to the invention.

Preferably said filamentous fungus is *Neurospora crassa*.

According to a yet further aspect of the invention there is provided a method for the production of pro-selected heterologous peptide from at least one filamentous fungus comprising:

a) providing either an expression cassette or expression/export cassette as aforedescribed;

b) transforming a pre-selected species of filamentous fungus with at least one of said cassettes;

c) culturing said transformed fungus; and d) harvesting said heterologous peptide.

It will be apparent from the above that when using the cbh-1 promoter, and the heterologous peptide production systems are grown on cellulose both good growth and induction of the expression of the induction system can be achieved.

According to a yet further aspect of the invention there is provided a protein having a cellulose-binding domain engineered in accordance with the invention.

According to a yet further aspect of the invention there is provided a filamentous fungus ideally *Neurospora crassa* capable of producing enhanced levels of cellulase enzyme complex in response to the presence of cellulose or cellobiose, which enhanced production is as a result of an increase in the copy number of the cellobiohydrolase gene or an increase in the strength of the associated promoter for the gene.

BRIEF DESCRIPTION OF THE DRAWINGS

The invention will now be described by way of example only with reference to the following Figures wherein;

FIGS. 1A–1D represents the nucleic acid (SEQ ID NO:1) and protein (SEQ ID NO:2) sequences of the cellobiohydrolase-1 *Neurospora crassa*. Some restriction enzyme sites and PCR primers are indicated. Important consensus sequences are underlined. Putative N-glycosylation sites are indicated by an asterisk. Intron sequence and non-coding sequences are in lower case;

FIGS. 3A–3C represents alignment of the *Neurospora crassa* cbh-1 protein sequence with related fungal cellulases. NCRX, HGRX, TRRX, TRVX, PHCX represent cbh-1 protein sequences of *Neurospora crassa* (SEQ ID NO:2), *H. grisea* (SEQ ID NO:3), *T. reesei* (SEQ ID NO:4), *T. viride* (SEQ ID NO:5) and *P. chrysosporium* (SEQ ID NO:7) respectively. TRRN represents the *T. reesei* EG 1 protein sequence (SEQ ID NO:6);

Cloning of the Cellobiohydrolase-1 Gene

The Neurospora cellobiohydrolase-1 gene, cbh-1, was cloned and sequenced using conventional methods such as sequence alignment of the gene from other species, design of nested PCR primers, and production of a fragment by PCR which was used to identify a genomic clone from a Neurospora genomic library in the vector lambda J1. The clone was sub-cloned into pBluescript, and sequenced by the dideoxy method.

The gene encodes a protein (see FIG. 1 (SEQ ID NO:2)) of approximately 550 amino acids including an export signal sequence between amino acids 1–28 approximately, a catalytic domain between amino acids 29–470 approximately, a hinge region between amino acids 471–519 approximately and a c-terminal cellulose-binding domain between amino acids 520–550.

Figure 3A:
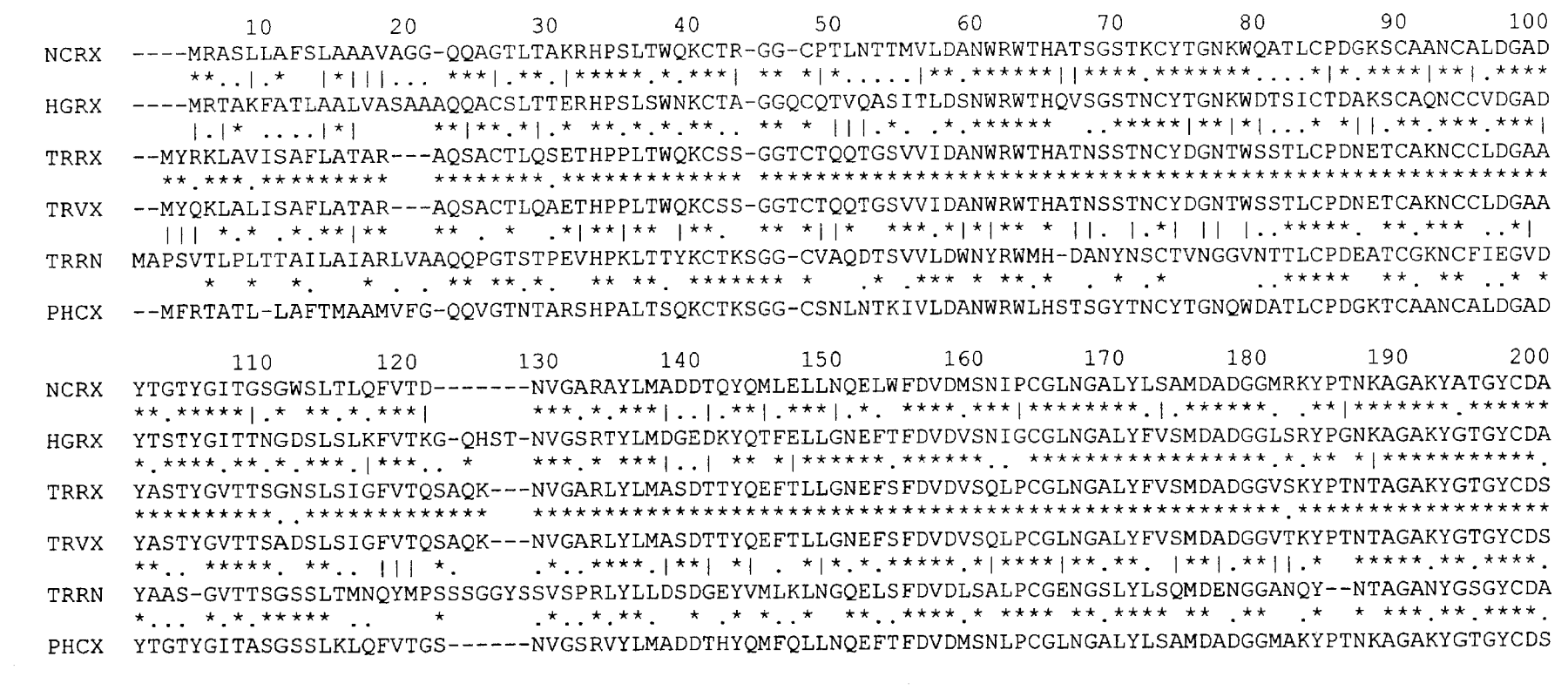

FIG. 3 shows an alignment of the cbh-1 amino acid sequence of the gene from *Neurospora crassa* when compared to corresponding genes from other organisms, from top to bottom, the sequence is as follows *N. crassa, H. grisea, T. reesei, T. viride, P. chrysosporium*.

Restriction Enzyme Mapping of Clone

Figure 2A:
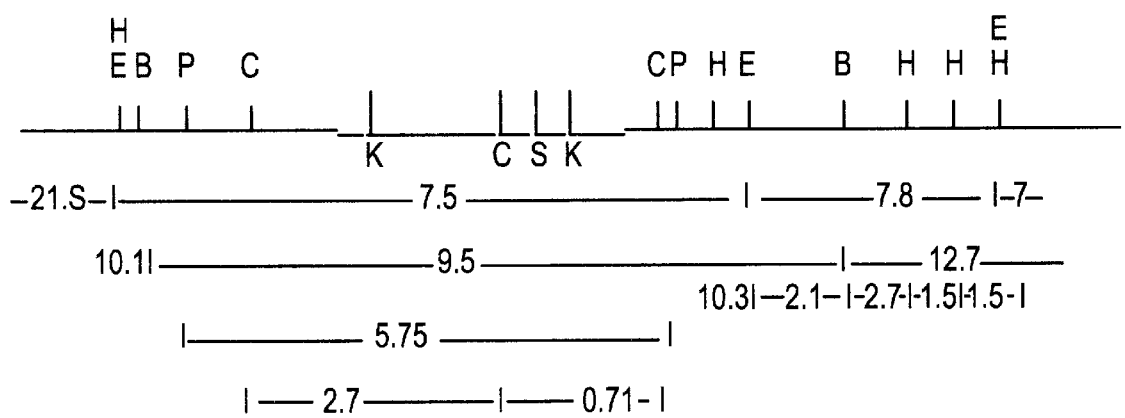
FIGS. 2A–2B represents the restriction map of the *Neurospora crassa* cbh-1 clone and in particular the restriction enzyme mapping of clone X (FIG. 2A), and the detailed restriction mapping of the region binding to the probes (FIG. 2B). The region binding to the probes is indicated in bold. P1 and P2 are PCR primers used for the amplification of the 0.8 Kb fragment ATG is the start codon of the cbh-1 gene. TAA is the stop codon of the cbh-1 gene. E=EcoR1, B=BamH1, H=Hind111, S=Sal1, P=Pst1, X=Xho1, K=Kpn1, C=Cla1. All sizes are in Kb.
Figure 2B:
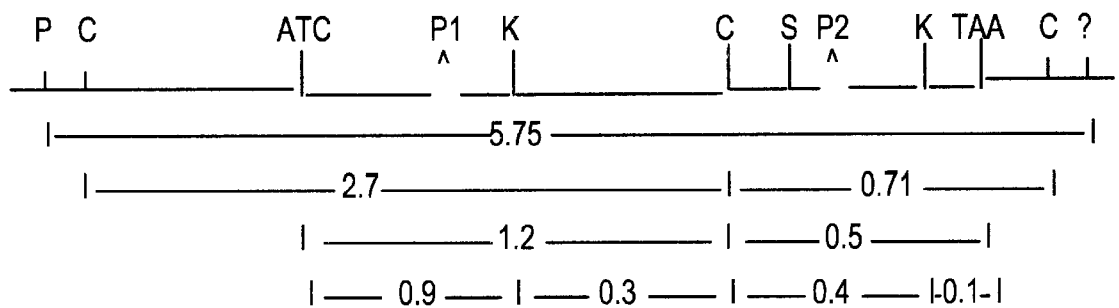
Figure 4A:
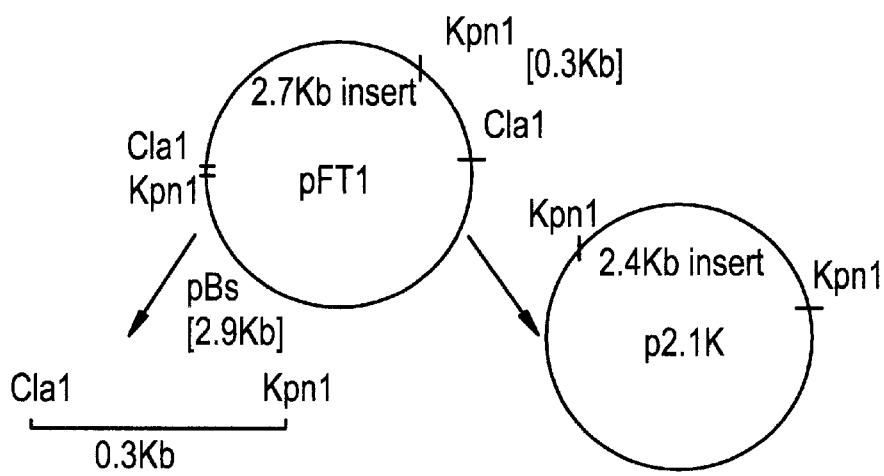
FIGS. 4A–4B represents the strategy used for the generation of plasmids.
Figure 4B:
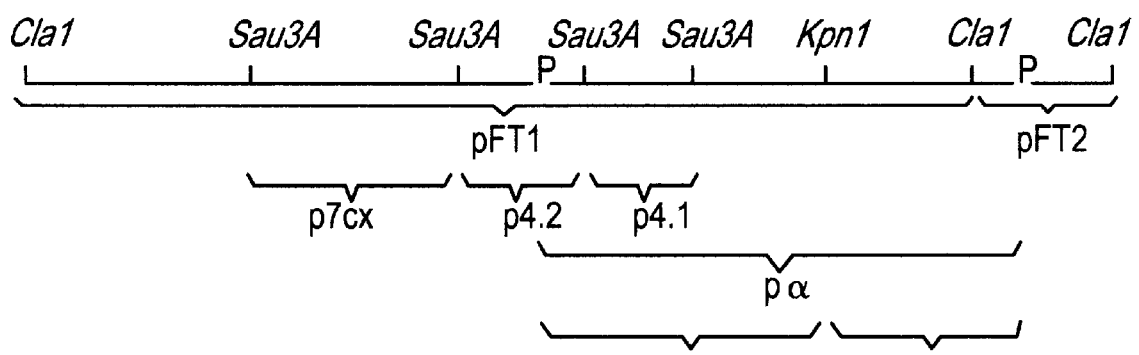

The restriction enzyme mapping of the clone is shown in FIG. 2. Moreover, in FIG. 4 the strategy for the generation of a new plasmid (p2.1 K) is shown towards the upper part of the Figure, and towards the lower part of the Figure the strategy for the generation of a set of new plasmids used during sequencing is shown.

Figure 5:
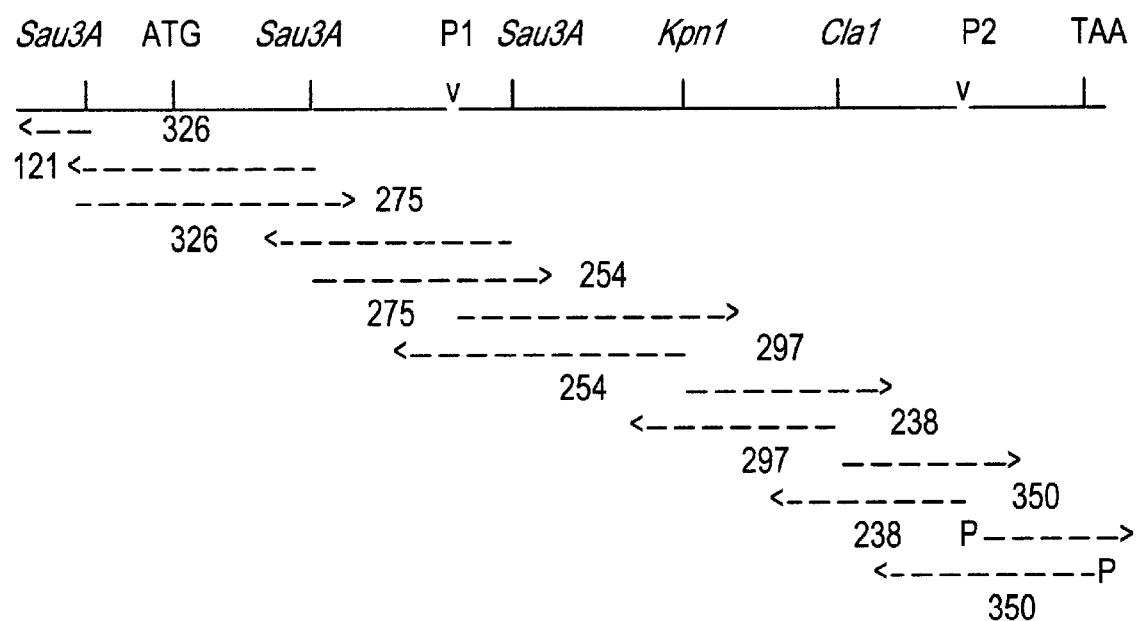
FIG. 5 represents the sequencing strategy of the cellobiohydrolase-1 gene of *Neurospora crassa*.

In FIG. 5 the sequencing strategy of the cellobiohydrolase-1 gene of *N. crassa* is shown.

Choice of Reporter Gene

Two obvious choices of reporter gene exist. The first of these is the well-characterised GUS β-glucuronidase) reporter gene available in the plasmid pNom123. This has the hph hygromycin-resistance gene as its Neurospora-selectable marker. An alternative reporter gene is the *Neurospora tyr* tyrosinase construct pTyr103 obtained from Dr S Free, SUNY, Buffalo. Another alternative reporter is pho-2 (acid phosphatase) of *Neurospora crassa*.

Isolation of the Essential Sequence of the Promoter

Experimental investigation of the limits of the essential promoter were undertaken by the cleavage of the sub-cloned promoter-reporter gene construct, and the deletion in from the 5'-end of the sub-clone. This involves either deletion of specific restriction fragments, subject to available restriction sites, or exonuclease degradation. In either case, the shortened "promoter" is relegated into the reporter construct and tested for residual promoter activity and regulation.

Experimental investigation of the limits of the essential promoter were undertaken by the cleavage of the sub-cloned promoter-reporter gene construct and the deletion in from the 5'-end of the sub-clone. This was done using mung bean exonuclease digestion. Alternatively, it could be done using any suitable restriction sites so as to provide a nested set of deletions. These deletions, or shortened promoter sequences, were relegated into a reporter construct and tested for residual promoter activity and regulation.

Transformation into Neurospora

Standard transformation methodology was used to effect the transformation of DNA constructs into Neurospora spheroplasts, using the cell wall-grading enzyme Novozym234 (Radford et al [1981] Molec Gen Genet 184, 567–569).

Selection of Transformants

Transformants were selected for pNom123 (the GUS reporter gene) by initial selection for hygromycin-resistance. Expression of the GUS activity was detected in a subsequent step by the development of blue color on X-gluc substrate.

With pTyr103, the derived plasmids with putative promoter inserts have no independent selectable marker. They were co-transformed with a second plasmid with a selectable marker, a process which gives circa 50% co-integration of the unselected plasmid. Although a number of co-selectable plasmids are suitable, an example would be pFB6 (Buxton and Radford [1984] Molec Gene Genet 190, 403–405), containing the cloned pyri-4 gene of Neurospora, selecting transformants by complementation of a pyrimidine-requiring recipient strain. Transformants thus selected demonstrated promoter activity from the cbh-1 promoter region by expression of tyrosinase activity in vegetative culture, tyrosinase only normally being active in the sexual phase of the life cycle. Tyrosinase activity is again detected colourimetrically, by the conversion of supplied L-tyrosine to black melanin pigment, or of L-DOPA to a soluble red pigment.

The red colour from L-DOPA, and the blue colour from X-gluc are both quantitatively assayable.

Isolation of the Essential Sequence of the Cellulose Binding Domain

Experimental investigation of the limits of the essential cellulose-binding domain were undertaken by the cleavage of the sub-clone cellulose-binding gene construct, and the deletion in from the 3'-end of the sub-clone. This involves either deletion of specific restriction fragments, subject to available restriction sites or exonuclease degradation. In either case, the shortened cellulose-binding domain is relegated into the reporter construct and tested for residual cellulose-binding activity.

Construction of an Expression Cassette

The expression constructs are of three types;

a) a transcriptional fusion, including the cbh-1 promoter and regulatory sequences upstream from a multi-cloning site, to allow the construction of transcriptional fusion with a coding sequence of any desired heterologous peptide. Such production would be intracellular, requiring subsequent purification of the product from a cell extract;

b) a translational fusion, including the cbh-1 promoter and export signal peptide in translational fusions, in all three possible reading frames, with the coding sequence of the desired heterologous peptide;

c) a translational fusion of a heterologous peptide near the c-terminal of the cbh- 1 with a proteolytic site in a linking region to allow subsequent cleavage of the heterologous peptide from the cbh-1. This would exploit the dispensable hinge and cellulose-binding domain of cbh-1, replacing this region with the other peptide.

An expression cassette developed using a cbh-1 promoter contains a replication origin from *E. coli,* an *E. coli*-selectable marker such as ampicillin-resistance, a Neurospora-selectable marker such as hygromycin-resistance, and the cbh-1 promoter/regulatory region upstream from a multi-cloning site. Such a construct was amplified in *E. coli,* transformed into *Neurospora crassa,* and used to express the inserted coding sequence in the *Neurospora crassa* mycalium, under cellulose induction if the promoter still had regulated expression.

Construction of an Expression Export Cassette

This construct was in many ways similar to the above expression cassette except in that it further incorporates a DNA sequence structure encoding a secretion signal. Moreover, it was a translational fusion, containing the cbh-1 signal sequence translationally fused to the n-terminal region of the coding sequence from the heterologous peptide. Because of the necessity to retain the function of the signal sequence and also a common reading frame through the fusion, three different constructs were required. In each case, the MCS was in a different reading frame, achieved by appropriate design of the ends of the synthetic MCS. Furthermore, care was needed in the design of the MCS to ensure the function of the export signal and the recognition and cleavage of the signal from the mature product in the process of maturation and secretion.

In this case, the heterologous product was both expressed and exported into the culture medium. This limits the range of peptides which can be made, but facilitates the purification of those compatible with this production method.

We claim:

1. A method of purifying a fusion protein containing a heterologous protein comprising:
   (a) transforming a host cell with an expression cassette encoding a fusion protein, wherein the fusion protein contains a C-terminal cellulose binding domain of a *Neurospora crassa* cellobiohydrolase-1, a linking region, and a heterologous protein; wherein the C-terminal cellulose binding domain of cellobiohydrolase-1 and the heterologous protein are linked together by the linking region; and wherein the host cell expresses the fusion protein;
   (b) contacting the fusion protein with a cellulose matrix; wherein the fusion protein binds to the cellulose matrix;
   (c) washing the cellulose matrix; and
   (d) eluting the fusion protein from the cellulose matrix; wherein the fusion protein is purified.

2. A method of purifying a heterologous protein comprising:
   (a) transforming a host cell with an expression cassette encoding a fusion protein wherein the fusion protein contains a C-terminal cellulose binding domain of a *Neurospora crassa* cellobiohydrolase-1, a linking region, and a heterologous protein; wherein the C-terminal cellulose binding domain of cellobiohydrolase-1 and the heterologous protein are linked together by the linking region; wherein the linking region contains a specific proteolytic cleavage site; and wherein the host cell expresses the fusion protein;

(b) contacting the fusion protein with a cellulose matrix; wherein the fusion protein binds to the cellulose matrix;

(c) washing the cellulose matrix; and (d) contacting the specific proteolytic cleavage site with a proteolytic protein that specifically recognizes the specific proteolytic cleavage site, and therein releases the heterologous protein from the cellulose matrix; wherein the heterologous protein is purified.

3. A method of immobilizing a heterologous protein on a cellulose matrix comprising contacting a fusion protein containing a C-terminal cellulose binding domain of a *Neurospora crassa* cellobiohydrolase-1, and a heterologous protein with a cellulose matrix; wherein the heterologous protein is immobilized on the cellulose matrix.

4. A method of using the immobilized heterologous protein of claim 3 as a biocatalyst comprising:

(a) contacting a substrate for the heterologous protein with the immobilized heterologous protein; and (b) collecting the product.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 1849 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Neurospora crassa
      (B) STRAIN: Oak Ridge 74A (vii) IMMEDIATE SOURCE:
      (A) LIBRARY: lambda J1
      (B) CLONE: X (ix) FEATURE:
     (A) NAME/KEY: CDS
     (B) LOCATION:join(152..832, 892..1758)

(ix) FEATURE:
     (A) NAME/KEY: intron
     (B) LOCATION:833..891

(ix) FEATURE:
     (A) NAME/KEY: exon
     (B) LOCATION:<152..832

(ix) FEATURE:
     (A) NAME/KEY: exon
     (B) LOCATION:892..>1761

(x) PUBLICATION INFORMATION:
    (A) AUTHORS: Taleb, F
             Radford, A
    (B) TITLE: Cloning sequencing and homologies of the
               CBH-1 (exocellobiohydrolase) gene of Neurospora
               crassa
    (K) RELEVANT RESIDUES IN SEQ ID NO: 1: FROM 1 TO 1849

(xi) SEQUENCE DESCRIPTION: SEQ ID NO: 1:

```
GAGTCTGTAA CCAAACTCTT TACCCGTCCT TGGGTCCCTG TAGCAGTATA TCCATTGTTT      60

CTTATATAAA GGTTAGGGGG TAAATCCCGG CGCTCATGAC TTCGCCTTCT TCCCTTATCT     120

GATCGGGCAC CGGAAACCAA TTGCACTCAA A ATG AGG GCC TCG CTC CTG GCC       172
                                  Met Arg Ala Ser Leu Leu Ala
                                   1               5

TTC TCC CTC GCT GCC GCC GTG GCC GGC GGC CAG CAG GCC GGC ACT CTC      220
Phe Ser Leu Ala Ala Ala Val Ala Gly Gly Gln Gln Ala Gly Thr Leu
            10              15                  20

ACC GCC AAG AGG CAC CCA TCC CTC ACA TGG CAG AAG TGC ACC AGG GGG      268
Thr Ala Lys Arg His Pro Ser Leu Thr Trp Gln Lys Cys Thr Arg Gly
 25              30                  35

GGG TGC CCG ACC CTG AAC ACC ACG ATG GTG CTC GAC GCG AAC TGG CGC      316
Gly Cys Pro Thr Leu Asn Thr Thr Met Val Leu Asp Ala Asn Trp Arg
 40              45                  50                      55

TGG ACT CAC GCC ACG TCC GGC TCC ACG AAG TGC TAC ACG GGC AAC AAG      364
Trp Thr His Ala Thr Ser Gly Ser Thr Lys Cys Tyr Thr Gly Asn Lys
                60                  65                  70

TGG CAG GCG ACG CTC TGC CCC GAT GGC AAG TCG TGC GCG GCG AAC TGC      412
Trp Gln Ala Thr Leu Cys Pro Asp Gly Lys Ser Cys Ala Ala Asn Cys
            75                  80                  85

GCG CTG GAC GGC GCC GAC TAC ACC GGC ACC TAC GGG ATC ACC GGG AGC      460
Ala Leu Asp Gly Ala Asp Tyr Thr Gly Thr Tyr Gly Ile Thr Gly Ser
            90                  95                 100

GGC TGG TCC CTC ACG CTC CAG TTC GTC ACG GAC AAC GTC GGC GCC CGT      508
Gly Trp Ser Leu Thr Leu Gln Phe Val Thr Asp Asn Val Gly Ala Arg
    105                 110                 115

GCC TAC CTG ATG GCG GAC GAC ACG CAG TAC CAG ATG TTG GAG CTC CTG      556
Ala Tyr Leu Met Ala Asp Asp Thr Gln Tyr Gln Met Leu Glu Leu Leu
120                 125                 130                 135

AAC CAG GAG TTG TGG TTC GAC GTC GAT ATG TCG AAC ATC CCG TGC GGT      604
Asn Gln Glu Leu Trp Phe Asp Val Asp Met Ser Asn Ile Pro Cys Gly
                140                 145                 150

CTG AAC GGC GCC CTC TAC CTC TCG GCG ATG GAC GCG GAT GGG GGC ATG      652
Leu Asn Gly Ala Leu Tyr Leu Ser Ala Met Asp Ala Asp Gly Gly Met
            155                 160                 165
```

| | | |
|---|---|---|
| AGG AAG TAC CCG ACC AAC AAG GCT GGC GCT AAG TAC GCT ACC GGT TAC | 700 | |
| Arg Lys Tyr Pro Thr Asn Lys Ala Gly Ala Lys Tyr Ala Thr Gly Tyr | | |
| 170              175             180 | | |

```
AGG AAG TAC CCG ACC AAC AAG GCT GGC GCT AAG TAC GCT ACC GGT TAC       700
Arg Lys Tyr Pro Thr Asn Lys Ala Gly Ala Lys Tyr Ala Thr Gly Tyr
        170                 175                 180

TGC GAC GCT CAG TGC CCC CGT GAT CTC AAG TAC ATC AAC GGT ATC GCC       748
Cys Asp Ala Gln Cys Pro Arg Asp Leu Lys Tyr Ile Asn Gly Ile Ala
185                 190                 195

AAC GTT GAG GGC TGG ACC CCT TCC ACC AAC GAT GCT AAC GGT ATT GGT       796
Asn Val Glu Gly Trp Thr Pro Ser Thr Asn Asp Ala Asn Gly Ile Gly
200                 205                 210                 215

GAC CAC GGA TCT TGC TGC TCT GAG ATG GAT ATC TGG GTTTGTTTGC            842
Asp His Gly Ser Cys Cys Ser Glu Met Asp Ile Trp
                220                 225

CGATTTTCCT TTCATCATTA GCATCACAGG TAACTAACAC CCACCTAAG GAA GCG         897
                                                      Glu Ala

AAC AAA GTC TCT ACA GCG TTC ACC CCG CAC CCC TGC ACC ACC ATC GAA       945
Asn Lys Val Ser Thr Ala Phe Thr Pro His Pro Cys Thr Thr Ile Glu
230                 235                 240                 245

CAG CAC ATG TGC GAG GGT GAC TCC TGC GGT GGT ACC TAT TCC GAC GAC       993
Gln His Met Cys Glu Gly Asp Ser Cys Gly Gly Thr Tyr Ser Asp Asp
                250                 255                 260

CGC TAT GGC GTA CTT TGC GAT GCC GAT GGT TGT GAC TTC AAC AGC TAC      1041
Arg Tyr Gly Val Leu Cys Asp Ala Asp Gly Cys Asp Phe Asn Ser Tyr
                265                 270                 275

CGC ATG GGC AAC ACC ACC TTC TAC GGT GAG GGC AAG ACT GTC GAT ACC      1089
Arg Met Gly Asn Thr Thr Phe Tyr Gly Glu Gly Lys Thr Val Asp Thr
                280                 285                 290

AGC TCC AAG TTC ACC GTT GTC ACC CAG TTC ATC AAG GAC TCC GCT GGC      1137
Ser Ser Lys Phe Thr Val Val Thr Gln Phe Ile Lys Asp Ser Ala Gly
295                 300                 305

GAT CTT GCT GAG ATC AAG GCC TTC TAC GTC CAG AAC GGA AAA GTC ATT      1185
Asp Leu Ala Glu Ile Lys Ala Phe Tyr Val Gln Asn Gly Lys Val Ile
310                 315                 320                 325

GAG AAC TCT CAG TCC AAC GTT GAT GGA GTT TCT GGC AAC TCC ATC ACC      1233
Glu Asn Ser Gln Ser Asn Val Asp Gly Val Ser Gly Asn Ser Ile Thr
                330                 335                 340

CAG TCT TTC TGC AAG TCT CAG AAG ACT GCT TTC GGC GAT ATC GAT GAC      1281
Gln Ser Phe Cys Lys Ser Gln Lys Thr Ala Phe Gly Asp Ile Asp Asp
                345                 350                 355

TTC AAC AAG AAG GGT GGC CTG AAG CAA ATG GGC AAG GCC CTT GCC CAA      1329
Phe Asn Lys Lys Gly Gly Leu Lys Gln Met Gly Lys Ala Leu Ala Gln
        360                 365                 370

GCC ATG GTC CTC GTC ATG TCC ATC TGG GAC GAC CAT GCC GCC AAC ATG      1377
Ala Met Val Leu Val Met Ser Ile Trp Asp Asp His Ala Ala Asn Met
        375                 380                 385

CTC TGG CTC GAC TCC ACC TAC CCT GTC CCG AAG GTC CCC GGT GCT TAC      1425
Leu Trp Leu Asp Ser Thr Tyr Pro Val Pro Lys Val Pro Gly Ala Tyr
390                 395                 400                 405

CGT GGC AGT GGC CCT ACC ACC TCG GGT GTC CCA GCT GAG GTC GAC GCC      1473
Arg Gly Ser Gly Pro Thr Thr Ser Gly Val Pro Ala Glu Val Asp Ala
                410                 415                 420

AAT GCT CCC AAC TCC AAG GTC GCC TTC TCC AAC ATC AAG TTC GGC CAC      1521
Asn Ala Pro Asn Ser Lys Val Ala Phe Ser Asn Ile Lys Phe Gly His
                425                 430                 435

CTC GGG ATC TCT CCT TTT AGC GGC GGC TCT TCC GGC ACC CCT CCT TCC      1569
Leu Gly Ile Ser Pro Phe Ser Gly Gly Ser Ser Gly Thr Pro Pro Ser
                440                 445                 450

AAC CCT TCG AGC TCC GCA AGC CCG ACT TCC TCC ACT GCT AAG CCT TCT      1617
Asn Pro Ser Ser Ser Ala Ser Pro Thr Ser Ser Thr Ala Lys Pro Ser
455                 460                 465
```

```
TCC ACC TCT ACT GCC TCC AAC CCC AGC GGT ACC GGT GCT GCT CAC TGG     1665
Ser Thr Ser Thr Ala Ser Asn Pro Ser Gly Thr Gly Ala Ala His Trp
470                 475                 480                 485

GCT CAG TGC GGT GGT ATT GGC TTC TCT GGC CCC ACC ACT TGC CCA GAG     1713
Ala Gln Cys Gly Gly Ile Gly Phe Ser Gly Pro Thr Thr Cys Pro Glu
                490                 495                 500

CCC TAC ACT TGC GCA AAA GAT CAC GAC ATT TAC TCC CAG TGC GTG         1758
Pro Tyr Thr Cys Ala Lys Asp His Asp Ile Tyr Ser Gln Cys Val
        505                 510                 515

TAAATTACTA GCCTGCTAGG GTAACCTTTT TGGTTCCTCT ACTACGGCAG CTAGGTGAAC   1818

TCGACTGCGA AGCAAAAAGG AACTTCGAGA A                                  1849

(2) INFORMATION FOR SEQ ID NO: 2:

(i) SEQUENCE CHARACTERISTICS:
        (A) LENGTH: 516 amino acids
        (B) TYPE: amino acid
        (D) TOPOLOGY: linear (ii) MOLECULE TYPE: protein (xi) SEQUENCE DESCRIPTION: SEQ ID NO: 2:

Met Arg Ala Ser Leu Leu Ala Phe Ser Leu Ala Ala Val Ala Gly
  1               5                  10                  15

Gly Gln Gln Ala Gly Thr Leu Thr Ala Lys Arg His Pro Ser Leu Thr
                 20                  25                  30

Trp Gln Lys Cys Thr Arg Gly Gly Cys Pro Thr Leu Asn Thr Thr Met
             35                  40                  45

Val Leu Asp Ala Asn Trp Arg Trp Thr His Ala Thr Ser Gly Ser Thr
 50                  55                  60

Lys Cys Tyr Thr Gly Asn Lys Trp Gln Ala Thr Leu Cys Pro Asp Gly
 65                  70                  75                  80

Lys Ser Cys Ala Ala Asn Cys Ala Leu Asp Gly Ala Asp Tyr Thr Gly
                 85                  90                  95

Thr Tyr Gly Ile Thr Gly Ser Gly Trp Ser Leu Thr Leu Gln Phe Val
                100                 105                 110

Thr Asp Asn Val Gly Ala Arg Ala Tyr Leu Met Ala Asp Asp Thr Gln
            115                 120                 125

Tyr Gln Met Leu Glu Leu Leu Asn Gln Glu Leu Trp Phe Asp Val Asp
130                 135                 140

Met Ser Asn Ile Pro Cys Gly Leu Asn Gly Ala Leu Tyr Leu Ser Ala
145                 150                 155                 160

Met Asp Ala Asp Gly Gly Met Arg Lys Tyr Pro Thr Asn Lys Ala Gly
                165                 170                 175

Ala Lys Tyr Ala Thr Gly Tyr Cys Asp Ala Gln Cys Pro Arg Asp Leu
                180                 185                 190

Lys Tyr Ile Asn Gly Ile Ala Asn Val Glu Gly Trp Thr Pro Ser Thr
            195                 200                 205

Asn Asp Ala Asn Gly Ile Gly Asp His Gly Ser Cys Cys Ser Glu Met
210                 215                 220

Asp Ile Trp Glu Ala Asn Lys Val Ser Thr Ala Phe Thr Pro His Pro
225                 230                 235                 240

Cys Thr Thr Ile Glu Gln His Met Cys Glu Gly Asp Ser Cys Gly Gly
                245                 250                 255

Thr Tyr Ser Asp Asp Arg Tyr Gly Val Leu Cys Asp Ala Asp Gly Cys
                260                 265                 270
```

```
Asp Phe Asn Ser Tyr Arg Met Gly Asn Thr Thr Phe Tyr Gly Glu Gly
        275                 280                 285

Lys Thr Val Asp Thr Ser Ser Lys Phe Thr Val Val Thr Gln Phe Ile
290                 295                 300

Lys Asp Ser Ala Gly Asp Leu Ala Glu Ile Lys Ala Phe Tyr Val Gln
305                 310                 315                 320

Asn Gly Lys Val Ile Glu Asn Ser Gln Ser Asn Val Asp Gly Val Ser
                325                 330                 335

Gly Asn Ser Ile Thr Gln Ser Phe Cys Lys Ser Gln Lys Thr Ala Phe
                340                 345                 350

Gly Asp Ile Asp Asp Phe Asn Lys Lys Gly Leu Lys Gln Met Gly
            355                 360                 365

Lys Ala Leu Ala Gln Ala Met Val Leu Val Met Ser Ile Trp Asp Asp
370                 375                 380

His Ala Ala Asn Met Leu Trp Leu Asp Ser Thr Tyr Pro Val Pro Lys
385                 390                 395                 400

Val Pro Gly Ala Tyr Arg Gly Ser Gly Pro Thr Thr Ser Gly Val Pro
                405                 410                 415

Ala Glu Val Asp Ala Asn Ala Pro Asn Ser Lys Val Ala Phe Ser Asn
                420                 425                 430

Ile Lys Phe Gly His Leu Gly Ile Ser Pro Phe Ser Gly Gly Ser Ser
            435                 440                 445

Gly Thr Pro Pro Ser Asn Pro Ser Ser Ser Ala Ser Pro Thr Ser Ser
        450                 455                 460

Thr Ala Lys Pro Ser Ser Thr Ser Thr Ala Ser Asn Pro Ser Gly Thr
465                 470                 475                 480

Gly Ala Ala His Trp Ala Gln Cys Gly Gly Ile Gly Phe Ser Gly Pro
                485                 490                 495

Thr Thr Cys Pro Glu Pro Tyr Thr Cys Ala Lys Asp His Asp Ile Tyr
            500                 505                 510

Ser Gln Cys Val
        515

(2) INFORMATION FOR SEQ ID NO:3:

(i) SEQUENCE CHARACTERISTICS:
        (A) LENGTH: 525 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: H. grisea (xi) SEQUENCE DESCRIPTION: SEQ ID NO:3:

Met Arg Thr Ala Lys Phe Ala Thr Leu Ala Ala Leu Val Ala Ser Ala
    1               5                   10                  15

Ala Ala Gln Gln Ala Cys Ser Leu Thr Thr Glu Arg His Pro Ser Leu
                    20                  25                  30

Ser Trp Lys Lys Cys Thr Ala Gly Gly Gln Cys Gln Thr Val Gln Ala
                35                  40                  45

Ser Ile Thr Leu Asp Ser Asn Trp Arg Trp Thr His Gln Val Ser Gly
            50                  55                  60

Ser Thr Asn Cys Tyr Thr Gly Asn Lys Trp Asp Thr Ser Ile Cys Thr
    65                  70                  75                  80
```

```
Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln Tyr Ser Thr Asn Val Gly Ser Arg Thr Tyr
            115                 120                 125

Leu Met Asp Gly Glu Asp Lys Tyr Gln Thr Phe Glu Leu Leu Gly Asn
            130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
            195                 200                 205

Glu Gly Trp Thr Gly Ser Thr Asn Asp Pro Asn Ala Gly Ala Gly Arg
            210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
            275                 280                 285

Asn Lys Thr Phe Tyr Gly Lys Gly Met Thr Val Asp Thr Thr Lys Lys
290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
            325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
            355                 360                 365

Lys Gly Gly Met Lys Gln Met Gly Lys Ala Leu Ala Gly Pro Met Val
            370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
            435                 440                 445

Gly Ser Thr Val Ala Gly Leu Pro Gly Ala Gly Asn Gly Gly Asn Asn
            450                 455                 460

Gly Gly Asn Pro Pro Pro Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495
```

```
            Cys Gly Gly Ile Gly Phe Thr Gly Pro Thr Gln Cys Glu Glu Pro Tyr
                            500                 505                 510

Thr Cys Thr Lys Leu Asn Asp Trp Tyr Ser Gln Cys Leu
                            515                 520                 525

(2) INFORMATION FOR SEQ ID NO:4:

(i) SEQUENCE CHARACTERISTICS:
        (A) LENGTH: 513 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: T.reesei (xi) SEQUENCE DESCRIPTION: SEQ ID NO:4:

Met Tyr Arg Lys Leu Ala Val Ile Ser Ala Phe Leu Ala Thr Ala Arg
         1               5                   10                  15

Ala Gln Ser Ala Cys Thr Leu Gln Ser Glu Thr His Pro Pro Leu Thr
                         20                  25                  30

Trp Gln Lys Cys Ser Ser Gly Gly Thr Cys Thr Gln Gln Thr Gly Ser
                         35                  40                  45

Val Val Ile Asp Ala Asn Trp Arg Trp Thr His Ala Thr Asn Ser Ser
         50                      55                  60

Thr Asn Cys Tyr Asp Gly Asn Thr Trp Ser Ser Thr Leu Cys Pro Asp
         65                      70                  75                  80

Asn Glu Thr Cys Ala Lys Asn Cys Cys Leu Asp Gly Ala Ala Tyr Ala
                         85                  90                  95

Ser Thr Tyr Gly Val Thr Thr Ser Gly Asn Ser Leu Ser Ile Gly Phe
                         100                 105                 110

Val Thr Gln Ser Ala Gln Lys Asn Val Gly Ala Arg Leu Tyr Leu Met
                         115                 120                 125

Ala Ser Asp Thr Thr Tyr Gln Glu Phe Thr Leu Leu Gly Asn Glu Phe
                         130                 135                 140

Ser Phe Asp Val Asp Val Ser Gln Leu Pro Cys Gly Leu Asn Gly Ala
         145                     150                 155                 160

Leu Tyr Phe Val Ser Met Asp Ala Asp Gly Gly Val Ser Lys Tyr Pro
                         165                 170                 175

Thr Asn Thr Ala Gly Ala Lys Tyr Gly Thr Gly Tyr Cys Asp Ser Gln
                         180                 185                 190

Cys Pro Arg Asp Leu Lys Phe Ile Asn Gly Gln Ala Asn Val Glu Gly
                         195                 200                 205

Trp Glu Pro Ser Ser Asn Asn Ala Asn Thr Gly Ile Gly Gly His Gly
                         210                 215                 220

Ser Cys Cys Ser Glu Met Asp Ile Trp Glu Ala Asn Ser Ile Ser Glu
         225                     230                 235                 240

Ala Leu Thr Pro His Pro Cys Thr Thr Val Gly Gln Glu Ile Cys Glu
                         245                 250                 255

Gly Asp Gly Cys Gly Gly Thr Tyr Ser Asp Asn Arg Tyr Gly Gly Thr
                         260                 265                 270

Cys Asp Pro Asp Gly Cys Asp Trp Asn Pro Tyr Arg Leu Gly Asn Thr
                         275                 280                 285

Ser Phe Tyr Gly Pro Gly Ser Ser Phe Thr Leu Asp Thr Thr Lys Lys
                         290                 295                 300
```

```
Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
            325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Arg Gly Thr Thr Thr Thr
450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
            485                 490                 495

Ala Ser Gly Thr Thr Cys Gln Val Leu Asn Pro Tyr Tyr Ser Gln Cys
            500                 505                 510

Leu (2) INFORMATION FOR SEQ ID NO:5:

(i) SEQUENCE CHARACTERISTICS:
        (A) LENGTH: 513 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: T. viride (xi) SEQUENCE DESCRIPTION: SEQ ID NO:5:

Met Tyr Gln Lys Leu Ala Leu Ile Ser Ala Phe Leu Ala Thr Ala Arg
1               5                   10                  15

Ala Gln Ser Ala Cys Thr Leu Gln Ala Glu Thr His Pro Pro Leu Thr
            20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
        50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
            85                  90                  95

Ser Thr Tyr Gly Val Thr Thr Ser Ala Asp Ser Leu Ser Ile Gly Phe
            100                 105                 110
```

```
Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Thr Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Ser Cys Gly Gly Thr Tyr Ser Gly Asp Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Asp Tyr Ser Gly Asn Ser Leu Asp Asp Asp Tyr Cys Ala Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asp Glu Thr Ser Ser Thr Pro Gly Ala Val Arg Gly Ser Ser Ser Thr
                405                 410                 415

Ser Ser Gly Val Pro Ala Gln Leu Glu Ser Asn Ser Pro Asn Ala Lys
            420                 425                 430

Val Val Tyr Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Pro Arg Pro Ala Thr Ser Thr Gly Ser Ser Pro Gly Pro Thr Gln Thr
465                 470                 475                 480

His Tyr Gly Gln Cys Gly Gly Ile Gly Tyr Ile Gly Pro Thr Val Cys
                485                 490                 495

Ala Ser Gly Ser Thr Cys Gln Val Leu Asn Pro Tyr Tyr Ser Gln Cys
            500                 505                 510

Leu
```

(2) INFORMATION FOR SEQ ID NO:6:

(i) SEQUENCE CHARACTERISTICS:
        (A) LENGTH: 459 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: T. reesei (xi) SEQUENCE DESCRIPTION: SEQ ID NO:6:

```
Met Ala Pro Ser Val Thr Leu Pro Leu Thr Thr Ala Ile Leu Ala Ile
 1               5                  10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
    195                 200                 205

Thr Ser His Gln Gly Phe Cys Cys Asn Glu Met Asp Ile Leu Glu Gly
210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335
```

```
            Leu Val Phe Ser Ile Trp Asn Asp Asn Ser Gln Tyr Met Asn Trp Leu
                    340                 345                 350

Asp Ser Gly Asn Ala Gly Pro Cys Ser Ser Thr Glu Gly Asn Pro Ser
                    355                 360                 365

Asn Ile Leu Ala Asn Asn Pro Asn Thr His Val Val Phe Ser Asn Ile
                    370                 375                 380

Arg Trp Gly Asp Ile Gly Ser Thr Thr Asn Ser Thr Ala Pro Pro Pro
            385                 390                 395                 400

Pro Pro Ala Ser Ser Thr Thr Phe Ser Thr Thr Arg Arg Ser Ser Thr
                            405                 410                 415

Thr Ser Ser Ser Pro Ser Cys Thr Gln Thr His Trp Gly Gln Cys Gly
                            420                 425                 430

Gly Ile Gly Tyr Ser Gly Cys Lys Thr Cys Thr Ser Gly Thr Thr Cys
                            435                 440                 445

Gln Tyr Ser Asn Asp Tyr Tyr Ser Gln Cys Leu
                            450                 455

(2) INFORMATION FOR SEQ ID NO:7:

(i) SEQUENCE CHARACTERISTICS:
        (A) LENGTH: 516 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: P. chrysosporium (xi) SEQUENCE DESCRIPTION: SEQ ID NO:7:

Met Phe Arg Thr Ala Thr Leu Leu Ala Phe Thr Met Ala Ala Met Val
            1               5                   10                  15

Phe Gly Gln Gln Val Gly Thr Asn Thr Ala Glu Asn His Arg Thr Leu
                            20                  25                  30

Thr Ser Gln Lys Cys Thr Lys Ser Gly Gly Cys Ser Asn Leu Asn Thr
                        35                  40                  45

Lys Ile Val Leu Asp Ala Asn Trp Arg Trp Leu His Ser Thr Ser Gly
                    50                  55                  60

Tyr Thr Asn Cys Tyr Thr Gly Asn Gln Trp Asp Ala Thr Leu Cys Pro
            65                  70                  75                  80

Asp Gly Lys Thr Cys Ala Ala Asn Cys Ala Leu Asp Gly Ala Asp Tyr
                            85                  90                  95

Thr Gly Thr Tyr Gly Ile Thr Ala Ser Gly Ser Ser Leu Lys Leu Gln
                            100                 105                 110

Phe Val Thr Gly Ser Asn Val Gly Ser Arg Val Tyr Leu Met Ala Asp
                            115                 120                 125

Asp Thr His Tyr Gln Met Phe Gln Leu Leu Asn Gln Glu Phe Thr Phe
                            130                 135                 140

Asp Val Asp Met Ser Asn Leu Pro Cys Gly Leu Asn Gly Ala Leu Tyr
            145                 150                 155                 160

Leu Ser Ala Met Asp Ala Asp Gly Gly Met Ala Lys Tyr Pro Thr Asn
                            165                 170                 175

Lys Ala Gly Ala Lys Tyr Gly Thr Gly Tyr Cys Asp Ser Gln Cys Pro
                            180                 185                 190

Arg Asp Ile Lys Phe Ile Asn Gly Glu Ala Asn Val Glu Gly Trp Asn
                    195                 200                 205
```

```
Ala Thr Ser Ala Asn Ala Gly Thr Gly Asn Tyr Gly Thr Cys Cys Thr
    210             215                 220

Glu Met Asp Ile Trp Glu Ala Asn Asn Asp Ala Ala Ala Tyr Thr Pro
225             230                 235                 240

His Pro Cys Thr Thr Asn Ala Gln Thr Arg Cys Ser Gly Ser Asp Cys
                245                 250             255

Thr Arg Asp Thr Gly Leu Cys Asp Ala Asp Gly Cys Asp Phe Asn Ser
            260             265                 270

Phe Arg Met Gly Asp Gln Thr Phe Leu Gly Lys Gly Leu Thr Val Asp
        275             280              285

Thr Ser Lys Pro Phe Thr Val Val Thr Gln Phe Ile Thr Asn Asp Gly
    290             295             300

Thr Ser Ala Gly Thr Leu Thr Glu Ile Arg Arg Leu Tyr Val Gln Asn
305             310             315                     320

Gly Lys Val Ile Gln Asn Ser Ser Val Lys Ile Pro Gly Ile Asp Leu
            325             330             335

Val Asn Ser Ile Thr Asp Asn Phe Cys Ser Gln Gln Lys Thr Ala Phe
            340             345             350

Gly Asp Thr Asn Tyr Phe Ala Gln His Gly Gly Leu Lys Gln Val Gly
        355             360             365

Glu Ala Leu Arg Thr Gly Met Val Leu Ala Leu Ser Ile Trp Asp Asp
    370             375             380

Tyr Ala Ala Asn Met Leu Trp Leu Asp Ser Asn Tyr Pro Thr Asn Lys
385             390             395                 400

Asp Pro Ser Thr Pro Gly Val Ala Arg Gly Thr Cys Ala Thr Thr Ser
            405             410             415

Gly Val Pro Ala Gln Ile Glu Ala Gln Ser Pro Asn Ala Tyr Val Val
            420             425             430

Phe Ser Asn Ile Lys Phe Gly Asp Leu Asn Thr Thr Tyr Thr Gly Thr
        435             440             445

Val Ser Ser Ser Val Ser Ser Ser His Ser Ser Thr Ser Thr Ser
    450             455             460

Ser Ser His Ser Ser Ser Ser Thr Pro Pro Thr Gln Pro Thr Gly Val
465             470             475             480

Thr Val Pro Gln Trp Gly Gln Cys Gly Gly Ile Gly Tyr Thr Gly Ser
            485             490             495

Thr Thr Cys Ala Ser Pro Tyr Thr Cys His Val Leu Asn Pro Tyr Tyr
            500             505             510

Ser Gln Cys Tyr
            515
```